US006753127B2

United States Patent
Han et al.

(10) Patent No.: US 6,753,127 B2
(45) Date of Patent: Jun. 22, 2004

(54) NORBORNENE-BASED COPOLYMER FOR PHOTORESIST, PREPARATION METHOD THEREOF, AND PHOTORESIST COMPOSITION COMPRISING THE SAME

(75) Inventors: Eun Sil Han, Daejun (KR); Bong Seok Moon, Daejun (KR); Jung Han Shin, Seoul (KR); Ouck Han, Daejun (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 10/246,474

(22) Filed: Sep. 19, 2002

(65) Prior Publication Data

US 2003/0118933 A1 Jun. 26, 2003

(30) Foreign Application Priority Data

Nov. 1, 2001 (KR) ........................................ 2001-67898

(51) Int. Cl.[7] .......................... G03F 7/038; C08F 4/06; C07C 49/105
(52) U.S. Cl. .................... 430/270.1; 430/326; 430/322; 430/327; 430/330; 430/905; 430/914; 430/910; 526/280; 549/367; 549/454; 568/374; 568/377
(58) Field of Search ............................. 430/270.1, 326, 430/322, 327, 330, 905, 910, 914; 526/280; 549/367, 454; 568/374, 377

(56) References Cited

U.S. PATENT DOCUMENTS

2003/0004289 A1 * 1/2003 Shin et al. ................... 526/171
2003/0194636 A1 * 10/2003 Wanat et al. ................ 430/191

FOREIGN PATENT DOCUMENTS

JP 2003183327 A * 7/2003 ........... C08F/32/08

* cited by examiner

Primary Examiner—Mark F. Huff
Assistant Examiner—Yvette C. Thornton
(74) Attorney, Agent, or Firm—Birch, Stewart, Kolasch & Birch, LLP

(57) ABSTRACT

Disclosed is an norbornene-based copolymer for photoresist, a preparation method thereof, and a photoresist composition comprising the same. The copolymer of the present invention exhibits high transparency to light of 193 nm wavelength and an excellent etching resistance, excellent resolution due to the remarkable difference between light-exposed part and light-unexposed part in the dissolving rate and excellent adhesion to the substrate due to very hydrophilic diketone group of its own. As a result, the copolymer of the present invention is very useful as ArF exposure photoresist material in the fabrication of semiconductor devices.

8 Claims, No Drawings

NORBORNENE-BASED COPOLYMER FOR PHOTORESIST, PREPARATION METHOD THEREOF, AND PHOTORESIST COMPOSITION COMPRISING THE SAME

BACKGROUND OF THE INVENTION

1. Field of the Invention

The present invention relates to a norbornene-based copolymer for photoresist, a preparation method thereof, and a photoresist composition comprising the same. More particularly, the present invention relates to the norbornene-based copolymer for photoresist, which is synthesized by use of a 5-norbornene-2-alkane-1,3-dione having pKa of about 5 (pKa of carboxylic acid) to about 10 (pKa of phenolic group) and its derivatives as essential comonomers and, optionally, ketal compound, which is a derivative of the above 5-norbornene-2-alkane-1,3-dione and the photoresist composition comprising the same.

2. Description of the Related Art

In general, photoresist for producing micropatterns must exhibit a low light-absorption to laser light of 193 nm wavelength, an excellent etching resistance, heat resistance and adhesion. And photoresists, which permit development in tetramethylammonium hydroxide (TMAH) solution, used recently in the fabrication of semiconductor devices, are advantageous for production cost. However, it is very difficult to produce photoresists to meet such various requirements.

To date, much effort has been made to obtain resin with high transparency to laser light of 193 nm wavelength and excellent etching resistance. For example, acrylic acid derivatives and methacrylic acid derivatives which have been widely used as base monomers of argon fluoride (ArF) exposure photoresist material have good transparency. However, they have disadvantage of poor etching resistance, such that the film produced therefrom cannot be served as masks.

As one of measures for improving etching resistance of ArF exposure photoresist material, there is an approach to introduce alicyclic olefin units to the side chain and the main chain of acryl-based copolymers. Introduction of alicyclic olefin units improves etching resistance of ArF exposure photoresist material, but is problematic in that, due to high acidity (pKa is about 5) of carboxyl group, which is a soluble functional group, the copolymer is dissolved faster than KrF exposure photoresist material having phenolic group (pKa is about 10) as a soluble functional group in alkaline developer solution, resulting in a pattern having an inferior profile, such as top loss profile. Top loss profile means the roundness of top of patterns while forming micropatterns.

Further more, carboxyl group has strong adhesion to TMAH, so that this method is problematic in that it may make patterns not tight due to swelling and if developer is used undiluted, the unexposed part is also dissolved.

Thus, to solve these problems, a study to introduce a ketal group of keto ester having the pKa more than 11 to ArF exposure photoresist have been conducted. This method reduces sensitivity to TMAH solution, resulting in the slowness of dissolving rate.

However, this method is problematic in that the pKa of keto ester substituted is too high to cause development in TMAH solution; as the mole fraction of keto ester substituted increases, the hydrophilicity of a resin is reduced and the adhesion of the resin to substrate is weakened, which make the formation of micropatterns difficult.

SUMMARY OF THE INVENTION

To cope with these problems, the present invention provides a photoresist copolymer having pKa of about 5 (pKa of carboxyl group) to about 10 (pKa of phenolic group) and a photoresist composition comprising the same, which is stable and can form excellent pattern profile by virtue of high resolution and remarkable substrate adhesion.

It is a feature of the present invention to provide a novel 5-norbornene-2-alkane-1,3-dione derivative, represented by the following Formula 1b:

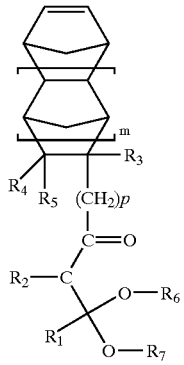

<Formula 1b> wherein $R_1$ is $C_{1-12}$ linear, branched or cyclic alkyl group;

$R_2$ is hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

$R_6$ and $R_7$ are independently $C_{1-6}$ alkyl group, or $R_6$ and $R_7$ are bonded with each other to form a ring;

p is an integer of 0 to 6; and m is 0 or 1.

It is another feature of the present invention to provide a preparation method of a 5-norbornene-2-alkane-1,3-dione derivative having the structure which is represented by the above Formula 1b, comprising transketalizing the 5-norbornene-2-alkane-1,3-dione which is represented by the following Formula 1a with a cyclic ketal or cyclic acetal compound in the presence of a acid catalyst in an organic solvent:

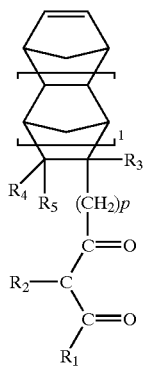

<Formula 1a> wherein $R_1$ is $C_{1-12}$ linear, branched or cyclic alkyl group;

$R_2$ is hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

p is an integer of 0 to 6; and l is 0 or 1.

It is still another feature of the present invention to provide a norbornene-based copolymer for photoresist, represented by the following Formula 3:

<Formula 3>

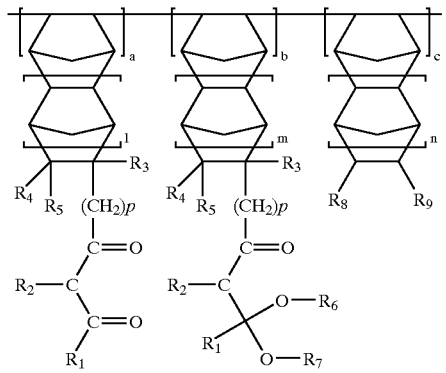

wherein $R_1$ is $C_{1-12}$ linear, branched or cyclic alkyl group;

$R_2$ is a hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

$R_6$ and $R_7$ are independently $C_{1-6}$ alkyl group, or $R_6$ and $R_7$ are bonded with each other to form a ring;

p is an integer of 0 to 6;

$R_8$ and $R_9$ are independently hydrogen atom, $C_{1-10}$ linear or branched alkyl group, $-(CH_2)_q-C(O)OR_{10}$, $-(CH_2)_q-OR_{10}$, $-(CH_2)_q-C(O)R_{10}$, $-(CH_2)_q-OC(O)R_{10}$, $-(CH_2)_q-OC(O)OR_{10}$ or $-(CH_2)_q-C(O)OCH_2OR_{10}$, in which $R_{10}$ is a hydrogen atom or $C_{1-10}$ linear, branched or cyclic alkyl group; q is an integer of 0 to 6; or $R_8$ and $R_9$ are bonded with each other to form a ring;

a, b and c independently satisfy $0.01 \leq a/(a+b+c) \leq 0.30$, $0 \leq b/(a+b+c) \leq 0.50$ and $0.20 \leq c/(a+b+c) \leq 0.99$; and l, m and n is each independently 0 or 1.

It is still another feature of the present invention to provide a preparation method of the copolymer of the Formula 3, which comprises the following steps:

(a) dissolving Pd(II) catalyst in a solvent selected from the group consisting of water, an organic solvent and a mixture thereof; and (b) adding the 5-norbornene-2-alkane-1,3-dione compound of the above Formula 1a, norbornene derivatives of the following Formula 2 and, optionally, derivatives of the above 5-norbornene-2-alkane-1,3-dione of the above Formula 1b as comonomers to the catalyst-dissolved solution and reacting the resultant mixture under non-activating gas stream or reduced pressure:

<Formula 1a>

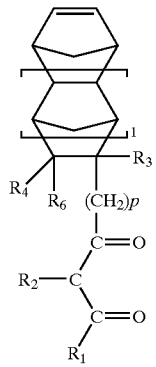

wherein $R_1$ is $C_{1-12}$ linear, branched or cyclic alkyl group;

$R_2$ is a hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

p is an integer of 0 to 6; and l is 0 or 1,

<Formula 1b>

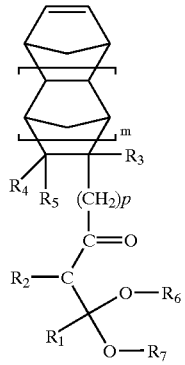

wherein $R_1$ is $C_{1-12}$ linear, branched or cyclic alkyl group;

$R_2$ is a hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

$R_6$ and $R_7$ are independently $C_{1-6}$ alkyl group, or $R_6$ and $R_7$ are bonded with each other to form a ring;

p is an integer of 0 to 6; and m is 0 or 1, and

<Formula 2>

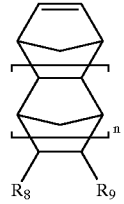

wherein $R_8$ and $R_9$ are independently hydrogen atom, $C_{1-10}$ linear or branched alkyl group, $-(CH_2)_q-C(O)$ $OR_{10}$, —$(CH_2)_q$—$OR_{10}$, —$(CH_2)_q$—C(O)$R_{10}$, —$(CH_2)_q$—OC(O)$R_{10}$, —$(CH_2)_q$—OC(O)$OR_{10}$ or —$(CH_2)_q$—C(O)OCH$_2$OR$_{10}$, in which $R_{10}$ is a hydrogen atom or $C_{1-10}$ linear, branched or cyclic alkyl group, q is an integer of 0 to 6, and $R_8$ and $R_9$ can be bonded with each other to form a ring; and n is 0 or 1.

It is still another feature of the present invention to provide a composition for photoresist comprising (a) the copolymer according to the Formula 3, (b) a photo acid generator, and (c) a solvent which can dissolve the components (a) and (b).

It is still another feature of the present invention to provide a preparation method of micropatterns, which comprises the following steps:

(a) coating a substrate with a photoresist composition to form a photoresist film;
(b) prebaking the coated substrate on a hot plate;
(c) exposing the prebaked film through a mask with radiation having a wavelength of 250 nm or less;
(d) postbaking the exposed film on a hot plate; and
(e) developing the postbaked film.

Other features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

Priority Korean Patent Application No. 2001-67898 filed Nov. 1, 2001 is incorporated herein in its entirety by reference.

The 5-norbornene-2-alkane-1,3-dione derivative of the present invention, which is represented by the following Formula 1b, is a kind of ketal compound:

<Formula 1b>

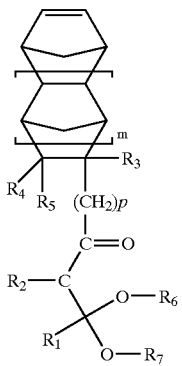

wherein $R_1$ is $C_{1-12}$ linear, branched or cyclic alkyl group;
$R_2$ is hydrogen atom or $C_{1-6}$ linear, branched or cyclic alkyl group;
$R_3$, $R_4$ and $R_5$ are independently hydrogen atom or $C_{1-6}$ linear or branched alkyl group, or $R_1$ and $R_5$ are bonded with each other to form a cyclic diketone;

$R_6$ and $R_7$ are independently $C_{1-6}$ alkyl group, or $R_6$ and $R_7$ are bonded with each other to form a ring;
p is an integer of 0 to 6; and
m is 0 or 1.

The 5-norbornene-2-alkane-1,3-dione derivative of the present invention can be synthesized by the following two methods. The first method is to transketalize the 5-norbornene-2-alkane-1,3-dione having the structure which is represented by the following Formula 1a with a cyclic ketal or cyclic acetal compound under acid catalyst in organic solvent:

<Formula 1a>

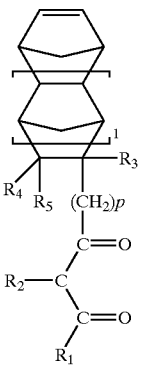

wherein $R_1$ is $C_{1-12}$ linear, branched or cyclic alkyl group;
$R_2$ is hydrogen atom or $C_{1-6}$ linear, branched or cyclic alkyl group;
$R_3$, $R_4$ and $R_5$ are independently hydrogen atom or $C_{1-6}$ linear or branched alkyl group, or $R_1$ and $R_5$ are bonded with each other to form a cyclic diketone;
p is an integer of 0 to 6; and
l is 0 or 1.

Examples of acid catalysts, useful for the above ketalization include organic acids such as camphorsulfonic acid, p-toluenesulfonic acid, pyridinium p-toluenesulfonate, oxalic acid, pyridinium chloride; inorganic acids such as hydrochloric acid, sulfuric acid, phosphoric acid and the like.

The addition amount of acid catalyst is determined without any specific restriction, and is generally 0.1~20 mol %, preferably 1~10 mol %, based on the above 5-norbornene-2-alkane-1,3-dione compound.

For non-limiting examples of organic solvents, available in the above ketalization, we can take one or more compounds selected from the group consisting of hydrocarbons such as toluene, xylene, benzene, cyclohexane, n-hexane, n-octane; halogenated hydrocarbons such as methylene chloride, dichloroethane, trichloroethylene, carbon tetrachloride, chloroform; esters such as methyl acetate, ethyl acetate, n-butyl acetate, methyl propionate; alcohol such as methanol, ethanol, n-propanol, iso-propanol, n-butanol, iso-butanol, t-butanol; ethers such as dimethyl ether, diethyl ether, diisopropyl ether, dimethoxy ethane, tetrahydrofuran, dioxane; N-methylpyrrolidone, N,N-diethylformamide, N,N-dimethylformamide, N,N-dimethylacetamide, dimethylsulfoxide, etc.

Besides, for non-limiting examples of the above cyclic ketal compounds, we can take 2,2-dimethyl-1,3-dioxolane, 1,4-dioxaspiro-[4,5]decane, 6,10-dioxaspiro-[4,5]decane, 2,2-dimethyl-1,3-dioxane, 2,2-diethyl-1,3-dioxane, 1,3-dioxane etc. The amount of the ketal or acetal chemical is 1~5 mole times as much as that of the above 5-norbornene-2-alkane-1,3-dione.

In the above transketalization, the reaction temperature is not particularly limited, and can employ from 0° C. to 150° C., preferably from 20° C. to 100° C.

The reaction time varies depending on the species of chemicals, those concentrations, and other reaction conditions. But, it is preferably from 1 to 10 hours.

The transketalization according to the present invention is advantageous in yield, since it escapes the side reaction of the water produced as a byproduct in the below-described general ketalization reactions.

The second method to synthesize the above 5-norbornene-2-alkane-1,3-dione derivative is to transketalize the 5-norbornene-2-alkane-1,3-dione, represented by the above Formula 1a with alkylalcohol or alkanediol under acid catalyst, if necessary, in organic solvent.

Examples of organic solvents useful for the ketalization include hydrocarbons such as toluene, xylene, benzene, cyclohexane, n-hexane and n-octane; halogenated hydrocarbons such as methylene chloride, dichloroethane, trichloroethylene, carbon tetrachloride and chloroform; ethers such as dimethyl ether, diethyl ether, diisopropyl ether, dimethoxy ethane, tetrahydrofuran and dioxane; N-methylpyrrolidone, N,N-dimethylformamide, N,N-dimethylacetamide, dimethylsulfoxide, and a combination of two or more of these solvents. It is preferable to use solvents, capable of removing the water from a reaction system by azeotropic distillation in the ketalization reaction.

Examples of alkyl alcohol, useful for the above ketalization include methanol, ethanol, propanol, butanol, pentanol, hexanol and Examples of alkanediol, useful for the above ketalization include ethylene glycol, propylene glycol, 2,2-dimethylpropane diol, 1,3-butanediol, 1,4-butanediol, diethylene glycol, dipropylene glycol, neopentyl glycol, 1,6-hexanediol, 2,2,4-trimethyl-1,6-hexanediol, triethylene glycol, 2-butyl-2-ethyl-1,3-propanediol, 1,2-cyclohexanediol, 1,3-cyclohexanediol and a combination of two or more of these alkanediols.

The amount of alcohol or diol is not particularly limited, and can employ from 1 to 20, preferably from 1.5 to 10 mole times to the above 5-norbornene-2-alkane-1,3-dione.

In the above ketalization, the reaction temperature is not particularly limited, and can employ from 0° C. to 150° C., preferably from 20° C. to 130° C.

After the above-mentioned transketalization or ketalization is completed, the resultant ketal compound can be directly used in a polymerization reaction without purification or separation, or it can be used in a polymerization reaction after separation and purification by extraction, recrystallization or other suitable conventional means.

A 5-norbornene-2-alkane-1,3-dione of the above Formula 1a, which is used to prepare the ketal compound of the present invention, can be prepared by reacting acetylnorbornene with ethylalkanoate in the presence of alkoxy sodium, if necessary, in the presence of an adequate solvent. The amount of ethylalkanoate is not particularly limited, and can employ from 1 to 30 mole times, preferably from 1 to 10 mole times to the acetylnorbornene.

From now on, we will describe, in detail, the norbornene-based copolymer for photoresist according to the present invention.

The norbornene-based copolymer for photoresist according to the present invention has the structure shown in the following Formula 3, and has its alicyclic cyclic units in its main chain:

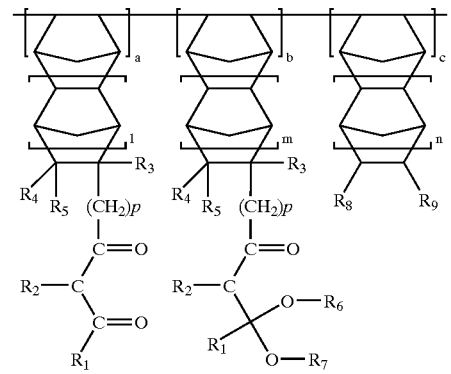

<Formula 3> wherein $R_1$ is $C_{1-12}$ linear, branched or cyclic alkyl group;

$R_2$ is a hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

$R_6$ and $R_7$ are independently $C_{1-6}$ alkyl group, or $R_6$ and $R_7$ are bonded with each other to form a ring;

p is an integer of 0 to 6;

$R_8$ and $R_9$ are independently hydrogen atom, $C_{1-10}$ linear or branched alkyl group, $-(CH_2)_q-C(O)OR_{10}$, $-(CH_2)_q-OR_{10}$, $-(CH_2)_q-C(O)R_{10}$, $-(CH_2)_q-OC(O)R_{10}$, $-(CH_2)_q-OC(O)OR_{10}$ or $-(CH_2)_q-C(O)OCH_2OR_{10}$, in which $R_{10}$ is a hydrogen atom or $C_{1-10}$ linear, branched or cyclic alkyl group, q is an integer of 0 to 6, and $R_8$ and $R_9$ can be bonded with each other to form a ring;

a, b and c independently satisfy $0.01 \leq a/(a+b+c) \leq 0.30$, $0 \leq b/(a+b+c) \leq 0.50$ and $0.20 \leq c/(a+b+c) \leq 0.99$; and l, m and n is each independently 0 or 1.

The molecular weight of the above norbornene-based copolymer is not particularly limited, and can employ from 1,000 to 300,000, preferably from 1,500 to 100,000, more preferably from 1,500 to 30,000.

According to the present invention, in the synthesis of the above norbornene-based copolymer, the 5-norbornene-2-alkane-1,3-dione compound of the above Formula 1a, and its derivatives of the following, are used as essential comonomers. Optionally, ketal compound of the above Formula 1b, and derivatives of the above 5-norbornene-2-alkane-1,3-dione can be used:

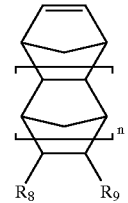

<Formula 2> wherein $R_8$ and $R_9$ are independently hydrogen atom, $C_{1-10}$ linear or branched alkyl group, $-(CH_2)_q-C(O)OR_{10}$, $-(CH_2)_q-OR_{10}$, $-(CH_2)_q-C(O)R_{10}$, $-(CH_2)_q-OC(O)R_{10}$, $-(CH_2)_q-OC(O)OR_{10}$ or $-(CH_2)_q-C(O)OCH_2OR_{10}$, in which $R_{10}$ is a hydrogen atom or $C_{1-10}$ linear, branched or cyclic alkyl group, q is an integer of 0 to 6, and $R_8$ and $R_9$ can be bonded with each other to form a ring; and n is 0 or 1.

Norbornene derivatives of the above Formula 2, which are used in the synthesis of copolymer of the present invention, can be synthesized, for example, by the Diels-Alder reaction of a cyclopentadiene with an adequately substituted dienophile. The general reaction equation is as follows:

<Reaction Formula 1>

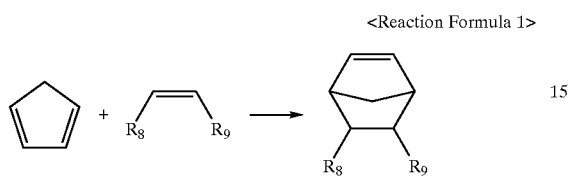

wherein $R_8$ and $R_9$ are the same groups that are defined in the above Formula 2.

The non-limiting examples of the available norbornene derivatives are norbornene, norbornene methanol, norbornene carboxylic acid, 5-norbornene-2-ethoxymethylcarboxylate, t-butyl-5-norbornene-2-carboxylate, di-t-butyl-5-norbornene-2-dicarboxylate, methyl-5-norbornene-2-carboxylate, isobornyl-5-norbornene-2-carboxylate, 2-hexyl-5-norbornene, 5-norbornene-2-methanol, 5-norbornene-2-ol, 5-norbornene-2,3-dimethanol, 5-oxa-tricyclo[5,2,1,0(2,6)]dec-8-en-3-one, etc.

As a polymerization method, whereby we obtain the norbornene copolymer of the present invention, we can use the radical polymerization, cationic polymerization, addition polymerization, or ring-opening polymerization to obtain the conventional multicyclic polymers such as norbornenes and its derivatives. But, it is preferable to use Pd(II)-catalyzed addition polymerization, for example, as shown in the following reaction equation 2;

<Reaction Formula 2>

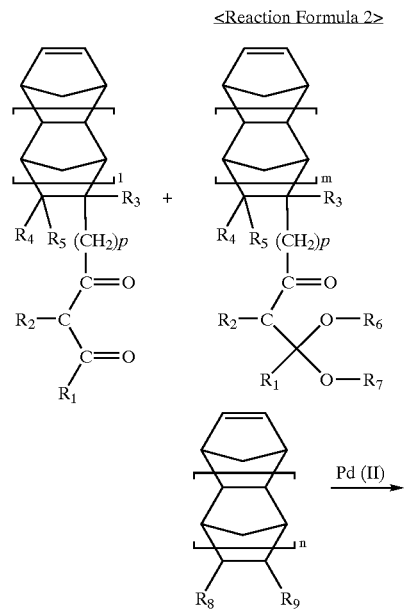

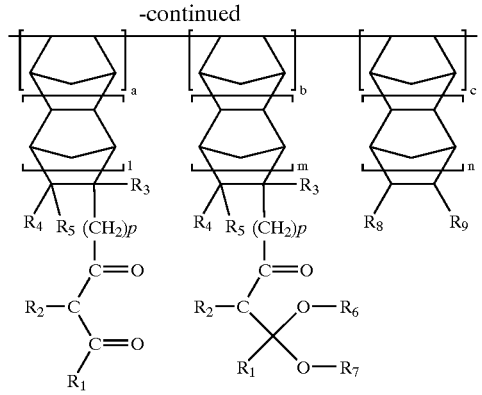

At this time, the above Pd(II) catalyst is represented by the following Formula 4a, 4b or 4c:

$PdX_2$                  <Formula 4a>

$(R'PdX)_2$            <Formula 4b>

$R''_n PdX_2$            <Formula 4c> wherein, X is a halogen atom or $C_{1\sim 10}$ alkyl group;

R' is a $C_{3-20}$ allyl group;

R" is a nitrile or a cyclodiene; and n is 1 or 2.

Detailed description of the preparation method of the norbornene copolymer of the present invention is as follows:

At first, the Pd(II) catalyst shown in the above Formulas 4a-4c as a polymerization initiator is dissolved in a solvent selected from the group consisting of water, an organic solvent and a mixture thereof. Next, to the above catalyst solution, are added the monomer of the above Formula 1a and the monomer of the above Formula 2 and, optionally, the monomer of the above Formula 1b. Then, polymerization is performed at a temperature of −50~80° C. for 0.5~48 hours under non-activating gas stream or reduced pressure. After completion of the polymerization, the resulting polymer can be purified through the known post-treatments.

In the above polymerization, a solvent selected from the group consisting of water, an organic solvent and a mixture thereof can be used as a polymerization solvent, wherein as an organic solvent, ether such as ethyl ether, 1,2-dimethoxyethane, tetrahydrofuran, 1,4-dioxane, 1,3-dioxolane; ketone such as methyl ethyl ketone, methyl isobutyl ketone, acetone, cyclohexanone; ester such as methyl acetate, ethyl acetate, n-butyl acetate; hydrocarbon such as benzene, toluene, xylene, etc can be used singly or in combination.

The feature of the novel norbornene-based copolymer, which is prepared by the above-mentioned method is to contain the monomer represented by the Formula 1a in the copolymer. In other words, the diketone of the 5-norbornene-2-alkane-1,3-dione, shown in the above Formula 1a has pKa values which is higher than that of the phenolic hydroxy group of the conventional novorac resin and phenol resin and is generally lower than that of the carboxylic group, i.e. the functional group of ArF exposure photoresist. Thus, during developing, it is easy to control the dissolution rate in a 2.23 weight % TMAH aqueous solution, which is a conventional alkaline developer solution. As a result, top loss and swelling of photoresist can be prevented and high resolution of photoresist can be achieved. Besides, diketones in light-unexposed area increase hydrophilicity of copolymer, thus increase adhesive force with substrate, as a result, provide excellent photoresist pattern.

Thus, norbornene-based copolymer of the present invention is very useful as a Deep UV(The wavelenth is same as or less than 250 nm) photoresist material.

Especially, if the copolymer of the present invention contains the monomer represented by the Formula 1b optionally, diketones are additionally provided by cleavage of ketal, i.e. protecting groups by the effect of the acid produced when exposed to light.

If the monomer having protected diketone, represented by the above Formula 1b as well as the monomer represented by the above Formula 1a are used as monomers to provide diketone to the copolymer of the present invention, we can control deprotection rate by acid and acidity after the deprotection, thus can achieve the high resolution due to the remarkable difference in dissolution rate between an exposed part and an unexposed part.

From now on, we will describe in detail the photoresist composition according to the present invention and the formation method of photoresist pattern thereby.

The present invention also provides a composition for photoresist comprising (a) a novel polymer for photoresist according to the present invention, (b) a photo acid generator, and (c) a solvent which can dissolve the components (a) and (b).

The concrete examples of photo acid generators, which can be used in the present invention are triphenylsulfonium trifluoromethanesulfonate, triphenylsulfonium perfluorooctanesulfonate, diphenyl-p-tolylsulfonium perfluorooctanesulfonate, tris(p-tolyl)sulfonium perfluorooctanesulfonate, tris(p-chlorobenzene)sulfonium tirfluoromethanesulfonate, tris(p-tolyl)sulfonium tifluoromethanesulfonate, trimethylsulfonium trifluoromethanesulfonate, dimethylphenylsulfonium trifluoromethanesulfonate, dimethyltolylsulfonium trifluoromethanesulfonate, dimethyltolylsulfonium perfluorooctanesulfonate, triphenylsulfonium p-toluenesulfonate, triphenylsulfonium methanesulfonate, triphenylsulfonium butanesulfonate, triphenylsulfonium n-octanesulfonate, triphenylsulfonium 1-naphthalenesulfonate, triphenylsulfonium 2-naphthalenesulfonate, triphenylsulfonium 10-camphorsulfonate, triphenylsulfonium 2,5-dichlorobenzenesulfonate, diphenyltolylsulfonium 1,3,4-trichlorobenzenesulfonate, dimethyl tolylsulfonium p-toluenesufonate, diphenyltolylsulfonium 2,5-dichlorobenzenesulfonate, 1-cyclohexylsulfonyl-1-(1,1-dimethylethylsulfonyl)diazomethane, bis(1,1-dimethylethylsulfonyl)diazomethane, bis(1-methylethylsulfonyl)methane, bis(cyclohexylsulfonyl)diazomethane, 1-cyclohexylsulfonyl-1-cyclohexylcarbonyldiazomethane, 1-diazo-1-cyclohexylsulfonyl-3,3'-dimethylbutane-2-one, 1-diazo-1-methylsulfonyl-4-phenylbutane-2-one, 1-diazo-1-(1,1-dimethylethylsulfonyl)-3,3-dimethyl-2-butanone, 1-acetyl-1-(1-methylethylsulfonyl)diazomethane, etc. The preferred content of photo acid generator is 0.1~10 parts by weight per the above copolymer resin 100 parts by weight.

For non-limiting examples of organic solvents, we can take one or more compounds selected from the group consisting of ethylene glycol monomethyl ether, ethylene glycol monoethyl ether, methyl Cellosolve acetate, ethyl Cellosolve acetate, diethylene glycol monomethyl ether, diethylene glycol monoethyl ether, propylene glycol methyl ether acetate, propylene glycol propyl ether acetate, diethylene glycol dimethyl ether, ethyl lactate, toluene, xylene, methyl ethyl ketone, cyclohexanone, 2-heptanone, 3-heptanone, 4-heptanone, etc. If necessary, as an assistant solvent, N-methylformamide, N,N-dimethylformamide, N-methylacetamide, N,N-dimethylacetamide, N-methylpyrrolidone, dimethylsulfoxide, alchol, etc can be further used. At this time, it is preferable to regulate the mixing ratio of an assistant solvent to be 10 or less weight % per the total solvent, and the mixing ratio of the gross solvent to be 70~95 weight % per the total composition.

The photoresist composition of the present invention comprises the above-described three components (the novel copolymer, the photoacid generator and the organic solvent). If necessary, a UV absorbent, a sensitivity controller (basic compound), a plasticizer, a organic acid, a surfactant can be contained as additives.

Preparation method of micropatterns using the photoresist composition of the present invention is as follows:

At first, a substrate such as a silicon wafer is coated with a photoresist composition to form a photoresist film. The coated substrate is prebaked on 60~150° C. high temperature plate for 60~180 seconds. The prebaked film is exposed through a mask to ArF excimer laser having a wavelength of 250 nm or less and a light intensity of 1~100 mJ/cm$^2$. The exposed film is postbaked on 60~150° C. high temperature plate for 60~180 seconds.

Thereafter the postbaked film is developed with a developer in the form of an aqueous base solution, for example, 0.1 to 5% of tetramethylammonium hydroxide (TMAH) for 30~180 seconds by conventional techniques such as dipping, puddling or spraying.

The present invention can be more clearly understood by reference to the following examples. It should be understood that the following examples are not intended to restrict the scope of the present invention in any manner.

In the following production examples and examples, the weight average molecular weight and the molecular weight distribution of the polymer are measured by GPC (gel permeation chromatography, solvent:THF, standard material:polystyrene)

PRODUCTION EXAMPLE 1

Synthesis of 5-norbornene-2-butane-1,3-dione (NBDO)

176.22 g(2 mol) of Ethylacetate and 108.04(2 mol) of methoxysodium(NaOMe) were dissolved in THF 1.5 l under nitrogen atmosphere, and 2-acetyl-5-norbornene 136.19 g(1 mol) was added slowly thereto through a dropping funnel for 1 hour, followed by a reaction at room temperature for 24 hours. After the completion of the reaction, the resultant mixture was extracted using water and ethyl acetate, and acid-treated. And, product was separated from it. The separated product layer was washed 3 times with water, dried over anhydrous magnesium sulfate, and then the solvent was distilled off under reduced pressure to provide 5-norbornene-2-butane-1,3-dione (NBDO) 125 g(yield: 70%, b.p.: 90~92° C./mmHg)

PRODUCTION EXAMPLE 2-1

Synthesis of 5-norbornene-2-(3-ethylene dioxy)-butane-1-one(NEDOBO):Method 1 (Transketalization)

To 35.6 g(200 mmol) of the 5-norbornene-2-butane-1,3-dione(NBDO) obtained in the production example 1 in 200 ml of benzene, 61.28 g(600 mmol) of 2,2-dimethyl-1,3-dioxolane and 0.38 g(2 mmol) of p-toluene sulfonic acid monohydrate were added. The reaction was carried out at room temperature for 4 hours.

After the completion of the reaction, the resultant mixture was washed with 1 M NaOH and water in turn, dried over anhydrous magnesium sulfate. The solvent was distilled off under reduced pressure to provide 177.6 g of 5-norbornene-2-(3-ethylene dioxy)-butane-1-one(NEDOBO) in 80% yield.

PRODUCTION EXAMPLE 2-2

Synthesis of 5-norbornene-2-(3-ethylene dioxy)-butane-1-one(NEDOBO):Method 2(Ketalization)

To 35.6 g(200 mmol) of the 5-norbornene-2-butane-1,3-dione(NBDO) obtained in the production example 1 in 200 ml of toluene, 37.2 g(600 mmol) of ethylene glycol and 0.38 g(2 mmol) of p-toluene sulfonic acid monohydrate were added. The reaction was carried out at room temperature for 4 hours while water i.e. byproduct was removed by dean stack.

After the completion of the reaction, the resultant mixture was washed with 1 M NaOH and water in turn, dried over anhydrous magnesium sulfate, and then the solvent was distilled off under reduced pressure to provide 31.08 g of 5-norbornene-2-3-ethylene dioxy)-butane-1-one (NEDOBO) in 70% yield.

PRODUCTION EXAMPLE 3-1

Synthesis of 5-norbornene-2-{(3-propylene dioxy)-butane-1-one}(NPDOBO):Method 1 (Transketalization)

A synthesis was conducted in a similar manner as in the Production Example 2-1 except for the use of 1,3-dioxane 52.87 g(600 mmol) in place of 2,2-dimethyl-1,3-dioxlane. 5-norbornene-2-{(3-propylene dioxy)-butane-1-one} (NPDOBO), the target product was obtained in 85% yield (200.6 g).

PRODUCTION EXAMPLE 3-2

Synthesis of 5-norbornene-2-{(3-propylene dioxy)-butane-1-one}(NPDOBO):Method 2(Ketalization)

A synthesis was conducted in a similar manner as in the Production Example 2-2 except for the use of 1,3-propanediol 45.66 g(600 mmol) in place of ethylene glycol as a diol. 5-norbornene-2-{(3-propylene dioxy)-butane-1-one}(NPDOBO), the target product was obtained in 70% yield (165 g).

PRODUCTION EXAMPLE 4

Synthesis of 5-norbornene-2-{(2',2'-dimethyl-3-propylene dioxy)-butane-1-one}(NDMPDOBO)

A synthesis was conducted in a similar manner as in the Production Example 3-2 except for the use of 2,2-dimethyl-1,3-propane diol 62.5 g(600 mmol) in place of 1,3-propanediol as a diol. 5-norbornene-2-{(2',2'-dimethyl-3-propylene dioxy)-butane-1-one}(NDMPDOBO), the target product was obtained in 60% yield (158.4 g).

EXAMPLE 1

Synthesis of Poly[NCA:NEMC:NBDO]=1:8:1 (Weight Ratio)

To 0.3 g of palladium chloride in $H_2O$:THF=1:1 mixed solvent, as comomomers, 27 g of 5-norbornene-2-carboxylic acid(NCA) and 3 g of the 5-norbornene-2-butane-1,3-dione (NBDO), obtained in the production example 1 were added. The reaction was performed under reduced pressure at about 40° C. for 24 hours. After the completion of the reaction, in order to remove Pd catalyst, the above reaction mixture was diluted with an adequate amount of THF solvent, and then was refluxed for about 5 hours under $H_2$ bubbling to provide dark precipitate.

Then, the dark precipitate was filtered out. The filtrate was poured to distilled water and the resultant precipitate was filtered and dried to provide Poly[NCA:NBDO]=9:1(weight ratio) 25.5 g(yield 85%). The weight-average molecular weight and the molecular weight distribution of the above copolymer are each 2,200 and 1.36.

Under $N_2$ atmosphere, To 30 g of the Poly[NCA:NBDO]= 9:1(weight ratio) in THF solvent, 19.4 g of triethylamine and 16.5 g of chloromethyl ethyl ether were added in turn, the reaction was performed at about 0° C. for 4 hours. After the completion of the reaction, the above reaction mixture was poured to distilled water and the resultant precipitate was filtered and dried to provide Poly[NCA:NEMC:NBDO]= 1:8:1(weight ratio) in 90% yield. The weight-average molecular weight and the molecular weight distribution of the above copolymer are each 4,000 and 1.55.

EXAMPLE 2

Synthesis of Poly[NCA:NEMC:NBDO]=1.5:7.5:2 (Weight Ratio)

A synthesis was conducted in a similar manner as in the Example 1 except for the use of, as copolymers, 24 g of 5-norbonrne-2-carboxylic acid and 6 g of 5-norbornene-2-butane-1,3-dione, which was obtained in the above production example 1 to provide 27 g of Poly[NCA:NBDO]=8:2 (weight ratio) in 90% yield. The weight-average molecular weight and the molecular weight distribution of the above copolymer are each 2,400 and 1.38. Subsequently, like the example 1, the above Poly[NCA:NBDO]=8:2(weight ratio) was dissolved in THF solvent, and then triethyl amine and chloromethyl ethyl ether were added thereto in turn. Then, the reaction was carried out to provide Poly [NCA:NEMC:NBDO]=1.5:7.5:2(weight ratio) in 93% yield. The weight-average molecular weight and the molecular weight distribution of the above copolymer are each 3,700 and 1.56.

EXAMPLE 3

Synthesis of Poly[NEMC:NBDO]=7:3(Weight Ratio)

A synthesis was conducted in a similar manner as in the Example 1 except for the use of, as copolymers, 21 g of 5-norbonrne-2-carboxylic acid and 9 g of 5-norbornene-2-butane-1,3-dione, which was obtained in the above Production Example 1 to provide 25.2 g of Poly[NCA:NBDO]= 7:3(weight ratio) in 84% yield. The weight-average molecular weight and the molecular weight distribution of the above copolymer are each 2,700 and 1.49. Subsequently, like the example 1, the above Poly[NCA:NBDO]=7:3 (weight ratio) was dissolved in THF solvent, and then triethyl amine and chloromethyl ethyl ether were added thereto in turn. Then, the reaction was carried out to provide Poly[NEMC:NBDO]=7:3(weight ratio) in 95% yield. The weight-average molecular weight and the molecular weight distribution of the above copolymer are each 3,500 and 1.49.

EXAMPLE 4

Synthesis of Poly[NCA:NEMC:NBDO:tBNCL]= 1:3:2:4 (Weight Ratio)

A synthesis was conducted in a similar manner as in the Example 1 except for the use of, as a copolymerizing catalyst, 0.5 g of palladium chloride, as copolymers, 10 g of 5-norbonrne-2-butane-1,3-dione which was obtained in the above Production Example 1 and 20 g of t-buthoxy-5-norbornene-2-carboxylate(tBNCL) to provide 45 g of Poly [NCA:NBDO:tBNCL]=4:2:4(weight ratio) in 90% yield. The weight-average molecular weight and the molecular weight distribution of the above copolymer are each 3,000 and 1.47. Subsequently, like the example 1, the above Poly[NCA:NBDO:tBNCL]=4:2:4(weight ratio) was dissolved in THF solvent, and then triethylamine and chloromethyl ethyle ether were added thereto in turn. Then, the reaction was carried out to provide Poly [NCA:NEMC:NBDO:tBNCL]=1:3:2:4(weight ratio) in 95% yield. The weight-average molecular weight and the molecular weight distribution of the above copolymer are each 3,400 and 1.55.

EXAMPLE 5

Synthesis of Poly[NCA:NEMC:NBDO:NB]= 0.5:5.5:2:2(Weight Ratio)

A synthesis was conducted in a similar manner as in the Example 1 except for the use of, as copolymers, 30 g of 5-norbonrne-2-carboxylic acid, 10 g of 5-norbonrne-2-butane-1,3-dione which was obtained in the above production example 1 and 10 g of norbornene(NB) to provide 45 g of Poly[NCA:NBDO:NB]=6:2:2(weight ratio) in 90% yield. The weight-average molecular weight and the molecular weight distribution of the above copolymer are each 3,100 and 1.46. Subsequently, like the example 1, the above Poly[NCA:NBDO:NB]=6:2:2(weight ratio) was dissolved in THF solvent, and then triethylamine and chloromethyl ether were added thereto in turn. Then, the reaction was performed to provide Poly[NCA:NEMC:NBDO:NB]= 0.5:5.5:2:2(weight ratio) in 96% yield. The weight-average molecular weight and the molecular weight distribution of the above copolymer are each 3,700 and 1.66.

EXAMPLE 6

Synthesis of Poly [NCA:NEMC:NBDO:tBNCL:NB]=1:2:1:5:1 (Weight Ratio)

A synthesis was conducted in a similar manner as in the Example 1 except for the use of, as copolymers, 15 g of 5-norbonrne-2-carboxylic acid, 5 g of 5-norbonrne-2-butane-1,3-dione which was obtained in the above production example 1, 25 g of t-butoxy-5-norbornene-2-carboxylate and 5 g of norbornene(NB) to provide 45 g of Poly[NCA:NBDO:tBNCL:NB]=3:1:5:1(weight ratio) in 90% yield. The weight-average molecular weight and the molecular weight distribution of the above copolymer are each 3,100 and 1.46. Subsequently, like the example 1, the above Poly[NCA:NBDO:tBNCL:NB]=3:1:5:1 was dissolved in THF solvent, and then triethylamine and chloromethyl ethyle ether were added thereto in turn. Then, the reaction was performed to provide Poly [NCA:NEMC:NBDO:tBNCL:NB]=1:2:1:5:1(weight ratio) in 94% yield. The weight-average molecular weight and the molecular weight distribution of the above copolymer are each 3,200 and 1.42.

EXAMPLE 7

Synthesis of Poly [NCA:NEMC:NBDO:NPDOBO:tBNCL]=1:1:2:3:3 (Weight Ratio)

A synthesis was conducted in a similar manner as in the Example 1 except for the use of, as copolymers, 10 g of 5-norbonrne-2-carboxylic acid, 10 g of 5-norbonrne-2-butane-1,3-dione which was obtained in the above production example 1, 15 g of 5-norbornene-2-{(3-propylene dioxy)-butane-1-one}, which was obtained in the above production example 3-1 and 15 g of t-butoxy-5-norbornene-2-carboxylate to provide 45 g of Poly [NCA:NBDO:NPDOBO:tBNCL]=2:2:3:3(weight ratio) in 90% yield. The weight-average molecular weight and the molecular weight distribution of the above copolymer are each 2,900 and 1.37. Subsequently, like the example 1, the above Poly[NCA:NBDO:NPDOBO:tBNCL]=2:2:3:3 (weight ratio) was dissolved in THF solvent, and then triethyl amine and chloromethyl ethyl ether were added thereto in turn. Then, the reaction was performed to provide Poly[NCA:NEMC:NBDO:NPDOBO:tBNCL]=1:1:2:3:3 (weight ratio) in 90% yield. The weight-average molecular weight and the molecular weight distribution of the above copolymer are each 3,100 and 1.39.

EXAMPLE 8

Synthesis of Poly[NBDO:NEDOBO:tBNCL]=2:6:2 (Weight Ratio)

Under $N_2$ atmosphere, to 0.3 g of palladium chloride in 15 g of $H_2O$:THF=1:1 mixed solvent, as comomomers, 6 g of t-buthoxy-5-norbornene-2-carboxylate, 18 g of the 5-norbornene-2-(3-ethylene dioxy)-butane-1-one, obtained in the Production Example 2 and 6 g of the 5-norbornene-2-butane-1,3-dione(NBDO), obtained in the Production Example 1 were added. The reaction was performed under reduced pressure at about 40° C. for 24 hours.

After the completion of the reaction, in order to remove Pd catalyst, the above reaction mixture was diluted with an adequate amount of THF solvent, and then was refluxed for about 5 hours under $H_2$ bubbling to provide dark precipitate.

At this time, the dark precipitate was filtered off. The filtrate was poured to distilled water and the resultant precipitate was filtered and dried to provide the target copolymer in 90% yield. The weight-average molecular weight and the molecular weight distribution of the above copolymer are each 2,800 and 1.4.

EXAMPLE 9

Synthesis of Poly[NBDO:NPDOBO:NB]=2:7:1 (Weight Ratio)

A synthesis was conducted in a similar manner as in the Example 8 except for the use of, as copolymers, 3 g of norbonrne, 6 g of 5-norbonrne-2-butane-1,3-dione which was obtained in the above production example 1 and 21 g of 5-norbornene-2-{(3-propylene dioxy)-butane-1 -one}, which was obtained in the above production example 3-1 to provide the target copolymer in 87% yield. The weight-average molecular weight and the molecular weight distribution of the above copolymer are each 2,900 and 1.38.

EXAMPLE 10

Synthesis of Poly [NBDO:NDMPDOBO:tBNCL:NB]=3:2:4:1 (Weight Ratio)

A synthesis was conducted in a similar manner as in the Example 8 except for the use of, as copolymers, 3 g of norbonrne, 12 g of t-buthoxy-5-norbornene-2-carboxylate, 9 g of 5-norbonrne-2-butane-1,3-dione which was obtained in the above production example 1 and 6 g of 5-norbornene- 2-{(2',2'-dimethyl-3-propylene dioxy)-butane-1-one}, which was obtained in the above production example 4 to provide the target copolymer in 85% yield. The weight-average molecular weight and the molecular weight distribution of the above copolymer are each 3,300 and 1.5.

EXAMPLE 11

Production of the Photoresist Compositon and Formation of Patterns 1 g of the each copolymer, which was obtained in the above examples 1~10 and, as a photoacid generator, 0.02 g of triphenylsulfonium trifluoromethane sulfonate were dissolved in 7 g of propylene glycol methyl ether acetate to provide a mixture. Then, the mixture was filtered using 0.1 μm filter. The filtrate was spin-coated on a silicon wafer and then prebaked on 120° C. high temperature plate for 60 seconds to form a photoresist film of the thickness of 0.4 μm. The wafer was exposed to light of 193 nm by use of an NA 0.7 light-exposure device in a light amount of 24 mj, then was heated at 120° C. for 60 seconds. Subsequently the exposed wafer was impregnated in 2.38 weight % TMAH aqueous solution for 60 seconds to provide positive photoresist patterns with the resolution of 0.11 μm L/S. The formed positive patterns exhibited excellent characteristics, such as the DOF of those is 0.5 μm, and the dose margin of those is ±2 mj.

As described in the above, the copolymer of the present invention exhibits high transparency to light of 193 nm wavelength and an excellent etching resistance, excellent resolution due to the remarkable difference between light-exposed part and light-unexposed part in the dissolving rate and excellent adhesion to the substrate due to very hydrophilic diketone group of its own. As a result, the copolymer of the present invention is very useful as ArF exposure photoresist material in the fabrication of semiconductor devices.

What is claimed is:

1. A 5-norbornene-2-alkane-1,3-dione derivative represented by the following Formula 1b:

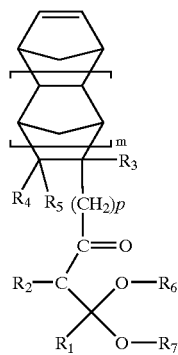

<Formula 1b> wherein $R_1$ is $C_{1-12}$ linear, branched or cyclic alkyl group;

$R_2$ is hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

$R_6$ and $R_7$ are independently $C_{1-6}$ alkyl group, or $R_6$ and $R_7$ are bonded with each other to form a ring;

p is an integer of 0 to 6; and m is 0 or 1.

2. A preparation method of a 5-norbornene-2-alkane-1,3-dione derivative including transketalization step of the 5-norbornene-2-alkane-1,3-dione having the structure which is represented by the following Formula 1a with a cyclic ketal or cyclic acetal compound under acid catalyst in organic solvent:

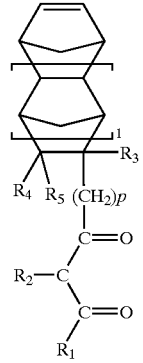

<Formula 1a> wherein $R_1$ is $C_{1-12}$ linear, branched or cyclic alkyl group;

$R_2$ is hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

p is an integer of 0 to 6; and l is 0 or 1.

3. A norbornene-based copolymer for photoresist, represented by the following Formula 3:

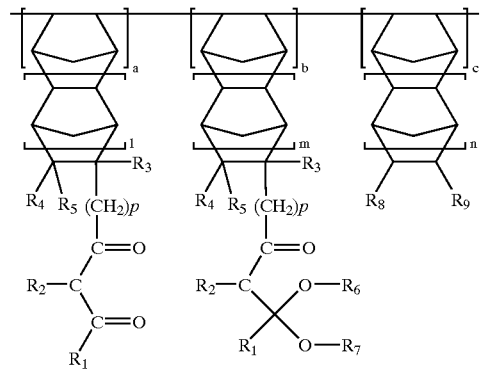

<Formula 3> wherein $R_1$ is $C_{1-12}$ linear, branched or cyclic alkyl group;

$R_2$ is a hydrogen atom or $C_{1-6}$ linear, branched or cyclic alkyl group;

$R_3$, $R_4$ and $R_5$ are independently hydrogen atom or $C_{1-6}$ linear or branched alkyl group, or $R_1$ and $R_5$ are bonded with each other to form a cyclic diketone;

$R_6$ and $R_7$ are independently $C_{1-6}$ alkyl group, or $R_6$ and $R_7$ are bonded with each other to form a ring;

p is an integer of 0 to 6;

$R_8$ and $R_9$ are independently hydrogen atom, $C_{1-10}$ linear or branched alkyl group, $-(CH_2)_q-C(O)OR_{10}$, $-(CH_2)_q-OR_{10}$, $-(CH_2)_q-C(O)R_{10}$, $-(CH_2)_q-OC(O)R_{10}$, $-(CH_2)_q-OC(O)OR_{10}$ or $-(CH_2)_q-C$ (O)OCH$_2$OR$_{10}$, in which R$_{10}$ is a hydrogen atom or C$_{1-10}$ linear, branched or cyclic alkyl group, q is an integer of 0 to 6, and R$_8$ and R$_9$ can be bonded with each other to form a ring;

a, b and c independently satisfy $0.01 \leq a/(a+b+c) \leq 0.30$, $0 \leq b/(a+b+c) \leq 0.50$ and $0.20 \leq c/(a+b+c) \leq 0.99$; and l, m and n is each independently 0 or 1.

4. The norbornene-based copolymer according to claim 3, wherein its molecular weight is 1,000~300,000.

5. A preparation method of the copolymer of the claim 3, including (a) dissolving Pd(II) catalyst in a solvent selected from the group consisting of water, an organic solvent and a mixture thereof and (b) adding the 5-norbornene-2-alkane-1,3-dione compound of the above Formula 1a, norbornene derivatives of the following Formula 2 and, optionally, derivatives of the above 5-norbornene-2-alkane-1,3-dione of the above Formula 1b as essential comonomers to the catalyst-dissolved solution and reacting the resultant mixture under non-activating gas stream or reduced pressure:

<Formula 1a>

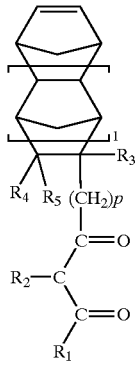

wherein R$_1$ is C$_{1-12}$ linear, branched or cyclic alkyl group;

R$_2$ is a hydrogen atom or C$_{1-6}$ linear, branched or cyclic alkyl group;

R$_3$, R$_4$ and R$_5$ are independently hydrogen atom or C$_{1-6}$ linear or branched alkyl group, or R$_1$ and R$_5$ are bonded with each other to form a cyclic diketone; and l is 0 or 1, <Formula 1b>

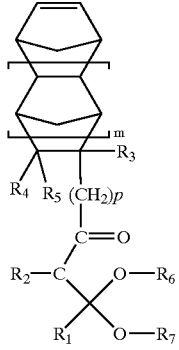

wherein R$_1$ is C$_{1-12}$ linear, branched or cyclic alkyl group;

R$_2$ is a hydrogen atom or C$_{1-6}$ linear, branched or cyclic alkyl group;

R$_3$, R$_4$ and R$_5$ are independently hydrogen atom or C$_{1-6}$ linear or branched alkyl group, or R$_1$ and R$_5$ are bonded with each other to form a cyclic diketone;

R$_6$ and R$_7$ are independently C$_{1-6}$ alkyl group, or R$_6$ and R$_7$ are bonded with each other to form a ring;

p is an integer of 0 to 6; and m is 0 or 1, and

<Formula 2>

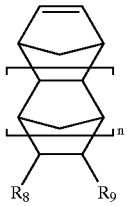

wherein R$_8$ and R$_9$ are independently hydrogen atom, C$_{1-10}$ linear or branched alkyl group, —(CH$_2$)$_q$—C(O)OR$_{10}$, —(CH$_2$)$_q$—OR$_{10}$, —(CH$_2$)$_q$—C(O)R$_{10}$, —(CH$_2$)$_q$—OC(O)R$_{10}$, —(CH$_2$)$_q$—OC(O)OR$_{10}$ or —(CH$_2$)$_q$—C(O)OCH$_2$OR$_{10}$, in which R$_{10}$ is a hydrogen atom or C$_{1-10}$ linear, branched or cyclic alkyl group, q is an integer of 0 to 6, and R$_8$ and R$_9$ can be bonded with each other to form a ring; and n is 0 or 1.

6. The preparation method of the copolymer of the claim 5, wherein the above Pd(II) catalyst is represented by the following Formula 4a, 4b or 4c:

PdX$_2$                                         <Formula 4a>

(R'PdX)$_2$                                 <Formula 4b>

R''$_n$PdX$_2$                                <Formula 4c>

Wherein, X is a halogen atom or C$_{1-10}$ alkyl group;

R' is a C$_{3-20}$ allyl group;

R'' is a nitrile or a cyclodiene; and n is 1 or 2.

7. A composition for photoresist comprising (a) the copolymer according to the claim 3, (b) a photo acid generator and (c) a solvent which can dissolve the components (a) and (b).

8. A preparation method of micropatterns comprising the steps of (a) coating a substrate with the photoresist composition according to the claim 7 to form a photoresist film;

(b) prebaking the coated substrate on a hot plate;

(c) exposing the prebaked film with radiation having a wavelength of 250 nm or less;

(d) postbaking the exposed film on a hot plate; and (e) developing the postbaked film.

* * * * *